(12) United States Patent
Khlystov et al.

(10) Patent No.: US 11,432,582 B2
(45) Date of Patent: Sep. 6, 2022

(54) ELECTRONIC CIGARETTE

(71) Applicant: Board of Regents of the Nevada System of Higher Education on behalf of the Desert Research Institute, Reno, NV (US)

(72) Inventors: Andrei Khlystov, Sparks, NV (US); Vera Samburova, Reno, NV (US); Marc Lynn Pitchford, Las Vegas, NV (US)

(73) Assignee: Board of Regents of the Nevada System of Higher Education on behalf of the Desert Research Institute, Reno, NV (US)

( * ) Notice: Subject to any disclaimer, the term of this patent is extended or adjusted under 35 U.S.C. 154(b) by 375 days.

(21) Appl. No.: 16/585,814

(22) Filed: Sep. 27, 2019

(65) Prior Publication Data
US 2020/0196679 A1 Jun. 25, 2020

Related U.S. Application Data

(60) Provisional application No. 62/784,264, filed on Dec. 21, 2018.

(51) Int. Cl.
*A24B 15/167* (2020.01)
*A61M 11/04* (2006.01)

(52) U.S. Cl.
CPC ......... *A24B 15/167* (2016.11); *A61M 11/042* (2014.02); *A61M 2205/3368* (2013.01)

(58) Field of Classification Search
CPC ............... A24B 15/167; A61M 11/042; A61M 2205/3368; A24F 40/10; A24F 40/03
See application file for complete search history.

(56) References Cited

U.S. PATENT DOCUMENTS

| | | | |
|---|---|---|---|
| 2013/0192620 A1* | 8/2013 | Tucker | A24F 40/70 131/329 |
| 2013/0255702 A1 | 10/2013 | Griffith, Jr. et al. | |
| 2014/0238605 A1 | 8/2014 | Mikami | |
| 2015/0027468 A1* | 1/2015 | Li | A24D 3/063 131/329 |

(Continued)

FOREIGN PATENT DOCUMENTS

| | | | | |
|---|---|---|---|---|
| CA | 3021371 A1 * | 1/2018 | | A24F 40/30 |
| TW | 202023403 | 7/2020 | | |
| WO | WO-2017149152 A1 * | 9/2017 | | A24B 15/16 |

OTHER PUBLICATIONS

International Search Report and Written Opinion in International application No. PCT/US2019/053872 dated Dec. 2, 2019, 9 pages.

*Primary Examiner* — Truc T Nguyen

(74) *Attorney, Agent, or Firm* — Knobbe, Martens, Olson & Bear, LLP

(57) ABSTRACT

Provided is an e-cigarette that includes a housing containing an atomizer, a first module and a second module. The first module can include a first e-liquid that is free, or substantially free, of flavorants. The second module can store a second e-liquid that includes flavorants. The atomizer can volatilize the first e-liquid by heating to form an aerosol at a high temperature. The heated aerosol can pass along a flow path from the first module into the second module. The second e-liquid can be volatilized at a low temperature within the second module by the heated aerosol.

22 Claims, 16 Drawing Sheets

(56) References Cited

U.S. PATENT DOCUMENTS

| | | | |
|---|---|---|---|
| 2015/0257447 A1* | 9/2015 | Sullivan | A61M 15/06 131/329 |
| 2015/0374035 A1 | 12/2015 | Sanchez et al. | |
| 2017/0049155 A1 | 2/2017 | Liu | |
| 2017/0112190 A1* | 4/2017 | Buchberger | A24F 42/60 |
| 2017/0265517 A1 | 9/2017 | Swede et al. | |
| 2018/0220704 A1 | 8/2018 | Best | |
| 2018/0310621 A1 | 11/2018 | Borkovec et al. | |
| 2020/0113244 A1* | 4/2020 | Novak, III | A24F 40/46 |
| 2021/0368864 A1* | 12/2021 | Ding | A24F 40/40 |

* cited by examiner

| Flavorant | Concentration (mg/ml) | | Ratio (enhanced/original) | Acceptable Enhanced Concentration Range |
|---|---|---|---|---|
| | E-liquid | Enhanced e-liquid | | |
| Maltol | 1.38 | 13.8 | 10 | 11–17 |
| Benzyl Alcohol | 2.24 | 22.4 | 10 | 18–27 |
| Ethyl Maltol | 4.50 | 90.0 | 20 | 72–108 |
| Vanillin | 3.71 | 185.5 | 50 | 148–223 |
| Ethyl Vanillin | 2.07 | 103.5 | 50 | 83–124 |
| Limonene | 1.72 | 25.8 | 15 | 21–31 |

FIG. 2D

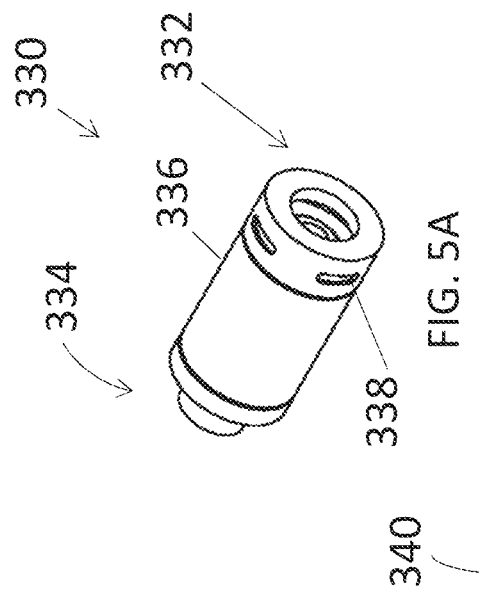
FIG. 5A
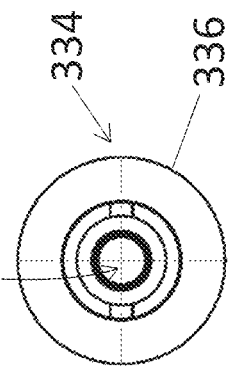
FIG. 5B
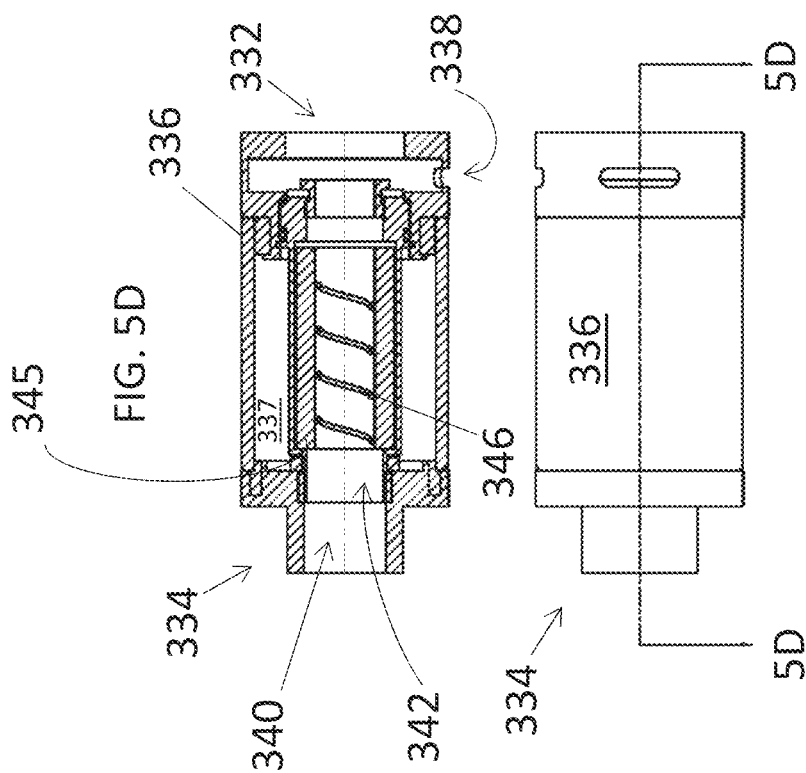
FIG. 5D
FIG. 5C

ELECTRONIC CIGARETTE

FIELD

This disclosure generally relates to electronic cigarettes, vape machines, and other vaping devices, referred to collectively herein as "e-cigarettes." In particular, this disclosure relates to methods and apparatus for decreasing the production of harmful chemicals in the aerosol formed by e-cigarettes.

BACKGROUND

E-cigarettes and vaping devices simulate the act of smoking tobacco in a conventional cigarette, cigar or pipe by producing an aerosol or vapor that is inhaled by a user. The aerosol mimics the physical sensation of inhaling tobacco smoke and reduces the health risks and other negative attributes of conventional smoking. The aerosol is produced by volatizing an e-liquid using heat or ultrasonic technology in an atomizer. E-liquids are typically a solution of carrier liquids, nicotine, and flavorants.

SUMMARY

While e-cigarettes can provide an alternative to smoking tobacco, the aerosols formed in conventional e-cigarettes and inhaled by users may still contain harmful compounds, such as, e.g., formaldehyde, acetaldehyde, acrolein and/or other members of the carbonyl group. Some of these emissions are due to the thermal decomposition of the flavorants used in e-liquids.

In one aspect of the present disclosure, an e-cigarette is provided that reduces the production of harmful compounds by heating flavorants to low temperatures only if heated at all. The e-cigarette can include a housing containing an atomizer, a first module and a second module. The first module can store a first e-liquid that is free, or substantially free, of flavorants. The second module can store a second e-liquid that includes flavorants. The atomizer can volatilize the first e-liquid by heating the first e-liquid to form an aerosol (or vapor) at a high temperature. The heated aerosol can pass along a flow path from the first module into the second module. The second e-liquid can be volatilized at a low temperature within the second module by the heated aerosol.

The foregoing summary is illustrative only and is not intended to be limiting. Other aspects, features, and advantages of the systems, devices, and methods and/or other subject matter described in this application will become apparent in the teachings set forth below. The summary is provided to introduce a selection of some of the concepts of this disclosure. The summary is not intended to identify key or essential features of any subject matter described herein.

The systems, methods and devices described herein have innovative aspects, no single one of which is indispensable or solely responsible for their desirable attributes. Without limiting the scope of the claims, some of the advantageous features will now be summarized.

BRIEF DESCRIPTION OF THE DRAWINGS

FIG. 2D is a chart showing concentrations of flavorant enhanced e-liquids;

FIG. 5A is a perspective view of a first module of the e-cigarette of FIG. 3;

FIG. 5B is an end view of the first module of FIG. 5A;

FIG. 5C is a side view of the first module of FIG. 5A;

FIG. 5D is a section view taken along the line 5D-5D in FIG. 5C;

DETAILED DESCRIPTION

The various features and advantages of the systems, devices, and methods of the technology described herein will become more fully apparent from the following description of the implementations illustrated in the figures. These implementations are intended to illustrate the principles of this disclosure, and this disclosure should not be limited to merely the illustrated examples. The features of the illustrated implementations can be modified, combined, removed, and/or substituted as will be apparent to those of ordinary skill in the art upon consideration of the principles disclosed herein.

Figure 1:
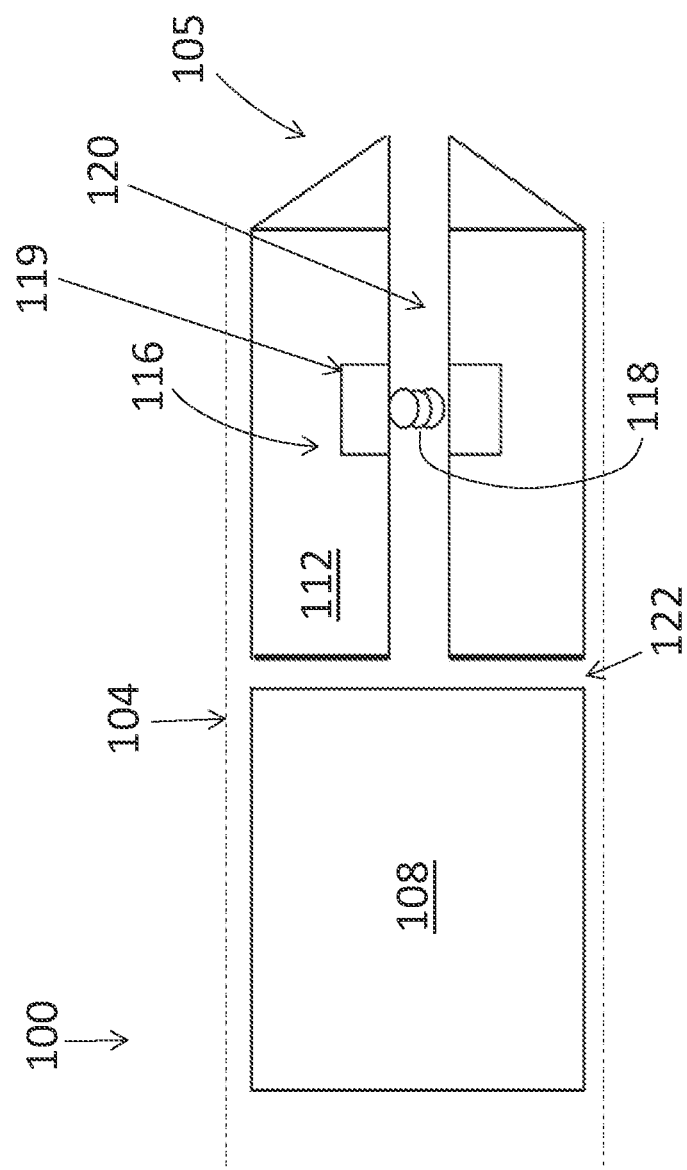
FIG. 1 is a schematic implementation showing the components of a conventional e-cigarette.

E-liquid is conventionally used in e-cigarettes, such as e-cigarette 100 shown in FIG. 1, to form the vapor or aerosol inhaled by a user and typically used to deliver nicotine into the airways of the user. The e-liquid is generally composed of a carrier liquid or base and various additives. The carrier liquid can be a liquid such as propylene glycol, vegetable glycerin, polyethylene glycol, water, ethanol, and/or other types of carrier liquids. Propylene glycol and vegetable glycerin are among the most common e-liquid carriers. Propylene glycol and vegetable glycerin are characterized typically as clear, faintly sweet and aromatic liquids. E-liquids may have various levels of viscosity. An e-liquid may have a high viscosity at room temperature to enable a long shelf life and to reduce leakage from a storage reservoir. Other additives can be included to form a gel or paste-like e-liquid.

Additives to the carrier liquid can include nicotine, nicotine salts, and/or any of various flavoring chemicals (flavorants) in varying concentrations. Common flavorants include, but are not limited to, maltol, benzyl alcohol, ethyl maltol, vanillin, ethyl vanillin, and limonene. Other common flavoring chemicals also commonly found in e-liquids include, but are not limited to, benzaldehyde, diacetyl, c-3-hexanol t-2-hexanol, benzaldehyde-pg-acetal, benzyl acetate, ethyl isovalerate, 2-methylbutyl acetate, and γ-decalactone. These flavorants are used to create e-liquid aerosols with flavor profiles and can be highly desirable for users. Commercial e-liquids include diverse flavor profiles and blends such as fruit flavors, candy flavors, desserts, milk, herbs, and spices.

FIG. 1 shows schematic components of a known e-cigarette 100. The e-cigarette 100 can include a housing 104. The housing 104 can contain a battery assembly 108. The battery assembly 108 can include a battery and one or more electronic connections for delivering power from the battery to an atomizer and/or other electronic controls for the e-cigarette 100. The e-cigarettes 100 can also variously include electronics, buttons, sensors, and indicator lights to assist in the operation and/or look of the e-cigarette (not shown).

The housing 104 can contain a reservoir 112 for holding an e-liquid. The housing 104 can contain an atomizer 116 for aerosolizing the e-liquid of the reservoir 112. The atomizer 116 can include a heating coil 118. The heating coils 118 can be connected with the battery and generate heat through internal resistance to a current flowing therethrough. The atomizer 116 can include a wick 119. The wick 119 can be formed of a wicking material such as a fibrous or foam material that can deliver the e-liquid from the reservoir 112 into contact with and/or adjacent to the heating coil 118. The wicking material can be thermally stable at the temperature reached by the heating coil 118 for at least a temporary period.

The housing 104 can include an airway 120. The airway 120 can include one or more air inlets 122. The airway 120 can be in communication with the atomizer 116. The airway 120 can extend through a mouthpiece 105. The mouthpiece 105 can be at one end of the housing. The user can draw air through the airway 120 at the mouthpiece 105.

The e-cigarette 100 can also include one or more control mechanisms for operating the atomizer 116 to form an aerosol from the e-liquid in the reservoir 112 using the atomizer 116. The control mechanisms can include a manual button operated by the user and/or one or more pressure sensors located along the airway 120 that automatically detect inhalation by the user at the mouthpiece 105.

In operation, a user can draw air, such as ambient air, into the airway 120 through the air inlet 122. The air can pass into the housing 104 and pass along the airway 120 to the atomizer 116. The wick 119 can deliver e-liquid to the heating coil 118 through capillary action and/or gravity, or other means. The control mechanism can deliver power to the heating coil 118 to vaporize the e-liquid in at least a portion of the wick 119 to form the aerosol or vapor. Temperatures in the atomizer 116 and/or on the heating coil 118 can be between approximately 150-275° C. or higher. The aerosol can mix with the air in the airway 120 and is carried to the user through the mouthpiece 105. By the time the aerosol reaches the mouthpiece 105, the aerosol has typically cooled to between 60° and 120° C. or lower. Various designs for the layout of the e-cigarette 100, the housing 104, the atomizer 116, the reservoir 112, the battery assembly 108, and the airway 120 are available commercially.

The high temperature heating of the e-liquid by the atomizer 116 (e.g., between approximately 150-275° C. or higher) can create secondary chemicals that are aerosolized with the e-liquid. As the user inhales the aerosol created by the atomizer 116, the user also inhales these secondary chemicals. Among these secondary chemicals are harmful chemicals such as members of the carbonyl family. The carbonyl family includes formaldehyde and acetaldehyde, both of which are known carcinogens. Because this effect represents a health risk to the user, one object of the present disclosure is to reduce the production of harmful chemicals.

FIG. 2 illustrates a two-stage e-cigarette 200 in schematic form. The e-cigarette 200 can include many of the same functionalities of the e-cigarette 100, with the differences noted herein. Similar components that are common between the 100 and 200 e-cigarette implementations are labeled with corresponding numbering in the 200 series.

The e-cigarette 200 can include a housing 204. The housing 204 can house a battery assembly 208 containing a battery for delivering power to an atomizer 216. The housing 204 can include a first module or chamber 210. The first module 210 can include a carrier reservoir 212 for storing a flavorless e-liquid. The flavorless e-liquid of the e-cigarette 200 differs from a conventional e-liquid in that it does not include, or is substantially free (e.g., less than about 1.00 mg/ml concentration) from flavorants. The flavorless e-liquid can be substantially free from any or all of maltol, benzyl alcohol, ethyl maltol, vanillin, ethyl vanillin, and limonene. In some implementations, the flavorless e-liquid will contain only a combination of propylene, glycol, vegetable glycerol, polyethylene glycol, nicotine, water, and/or ethanol. The flavorless e-liquid can include nicotine and/or nicotine salts.

The first module 210 can include the atomizer 216. The atomizer 216 can include a heating coil 218. The heating coil 218 can be electrically coupled with the battery. A wick 219 can deliver the flavorless e-liquid from the reservoir 212 to the heating coil 218. The battery assembly 208 can be configured to deliver energy into the atomizer 216 such as through the heating coil 218 to vaporize or atomize the flavorless e-liquid from the reservoir 212. An airway 220 can draw air through the first module 210 from one or more inlets 222 and exit the housing 204 at a mouthpiece 205.

The housing 204 can further include a second module or chamber 230. The second module 230 can be adjacent to the first module 210. The first and second modules 210, 230 can be connected directly or indirectly (e.g., via one or more aerosol nozzles). The airway 220 can extend from the first module 210 to the second module 230. The second module 230 can be downstream of the first module 210 and air inlets 222. The second module 230 can be located between the mouthpiece 205 and the atomizer 216. In other implementations, the second module 230 is an integral unit with the first module 210 and/or is upstream of the atomizer 216.

The second module 230 can include a flavorant reservoir 232. The second reservoir can house a flavored e-liquid. The flavored e-liquid can include one or more carrier liquids and any or all of the flavorants: benzyl alcohol, ethyl maltol, vanillin, ethyl vanillin, limonene, and/or other flavorings. The flavored e-liquid in a reservoir 232 can include any of the carriers such as the propylene, glycol, vegetable glycerol, water, and/or ethanol.

The second module 230 can include a delivery mechanism 234. The delivery mechanism 234 can be located adjacent to and/or within the airway 220. The delivery mechanism 234 may comprise a chamber within the second module 230. The airway 220 can pass through one or more nozzles to enter and exit the chamber. For example, the airway 220 can follow a tortuous path through the chamber of the second module 230. The delivery mechanism 234 can comprise a porous material. The delivery mechanism 234 can comprise a permeable material or membrane formed of plastic, mineral, glass, metal, fiber (synthetic or natural) or any other suitable material that can at least temporarily contain the flavored e-liquid and expose the flavored e-liquid to air and/or vapor passing through the airway 220 on its way to the mouthpiece 205. The delivery mechanism 234 can comprise a sleeve. The airway 220 can pass through the sleeve. The delivery mechanism 234 can comprise a foam, a sponge, or other permeable membrane. The delivery mechanism 234 can comprise a plastic, rubber, cellulose, wood pulp, fibrous material (synthetic or natural), mineral, metallic and/or any other suitable material. The delivery mechanism 234 can comprise a smooth inner surface of the chamber, a textured inner surface of the chamber, and/or one or more grooves or slots.

The second module 230 can include one or more apertures, wicks, or other delivery mechanisms to fill the delivery mechanism 234 with flavored e-liquid from the reservoir 232. The delivery mechanism 234 can include the flavored e-liquid in the form of a gel or dissolved in a permeable membrane or substrate through which aerosol and/or air must pass along the airway 220. The airway 220 through the delivery mechanism 234 can follow a tortuous path.

In some implementations, the second module 230 does not include a separate reservoir 232; only the delivery mechanism 234 contains the flavored e-liquid. Optionally, the second module 230 can include a second atomizer that operates at a reduced temperature than the atomizer 216 (e.g., in the range of about 70° C. to about 150° C.). A wick can deliver the flavored e-liquid to the second atomizer. The delivery mechanism 234 (e.g., wick material) need not be as thermally stable as the wick 219 because it is generally exposed to lower temperatures than those of the coil 218.

In operation, the atomizer 216 can create an aerosol or vapor from a carrier or flavorless e-liquid delivered from the carrier reservoir 212 through the wick 219. The heating coil 218 can atomize the flavorless e-liquid. Air can be drawn in through the inlet 222 along the airway 220. The air can carry the aerosol from the atomizer 216 into the second module 230. The heated aerosol can contact the delivery mechanism 234. Flavorants contained therein can volatilize and be picked up within the aerosol. The aerosol can then continue along the airway 220 to the mouthpiece 205.

Figure 2A:
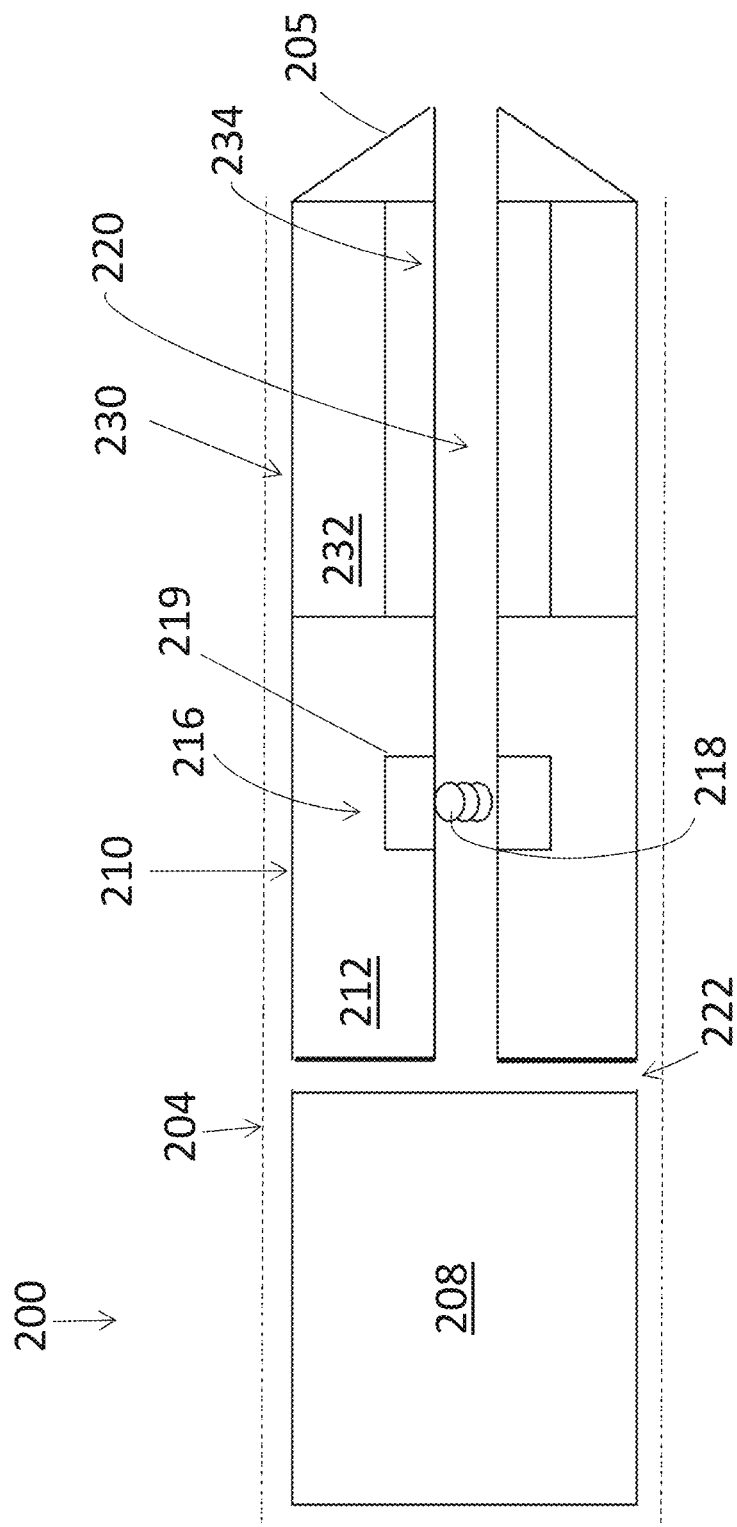
FIG. 2A is a schematic implementation showing the components of a two-stage e-cigarette.
Figure 2B:
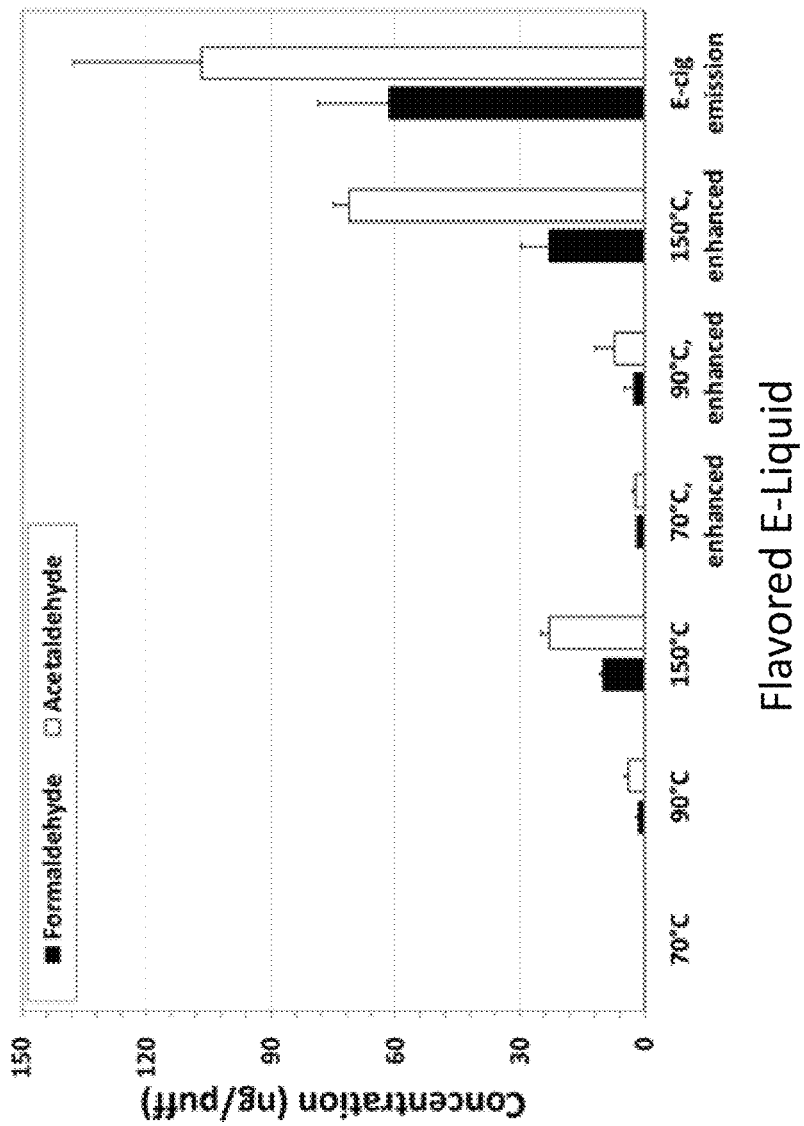
FIG. 2B is a chart showing a concentration of formaldehyde production for e-liquids aerosolized at different temperatures.

Various arrangements for the delivery mechanism 234 are possible. The aerosol created by the atomizer 216 can be heated to an elevated temperature. Passage of the heated aerosol through the delivery mechanism 234 can heat and volatilize the flavored e-liquid. This heating of the flavored e-liquid can take place at temperatures below the high temperatures of the atomizer 216. The temperatures of the aerosol within the second module 230 can be in the range of about 70° C. to about 150° C. When heated within this temperature range, flavorants have been found to produce fewer harmful secondary chemicals, such as formaldehyde and acetaldehyde. FIG. 2B illustrates experimental results showing the reduction in formaldehyde and acetaldehyde produced by heating a flavored e-liquid to temperatures below conventional e-cigarette atomizer temperatures for common-use vaping topography (i.e., 1.5LPM, 4-second sampling puff duration). In one example, less than 30 nanograms of formaldehyde per puff are produced for the common-use vaping topography.

In this manner, the flavorants can be delivered to the user to enhance the act of smoking the e-cigarette 200 without undergoing heating directly by the atomizer 216. The effect of the two-stage arrangement of the e-cigarette 200 is the decreased production of harmful secondary chemicals. By eliminating or reducing the flavoring chemicals in the e-liquid that are delivered to the atomizer 216, the heating process of the atomizer does not produce as many harmful secondary chemicals. Moreover, this concept of separating the flavoring chemicals from the high temperature atomization and aerosolization process has applications outside of e-cigarettes. It can also be used in other thermal air dispensing systems such as air fresheners and/or other aerosolization devices.

Figure 2C:
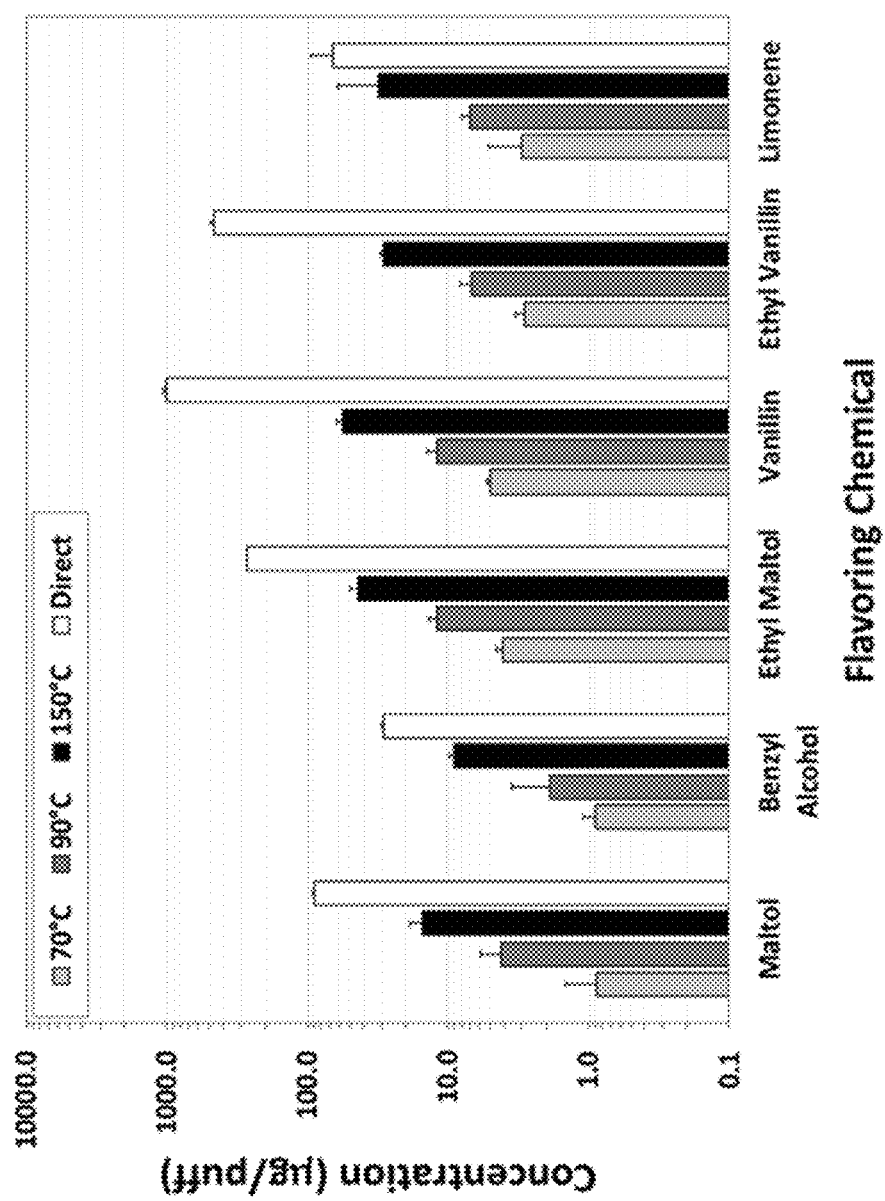
FIG. 2C is a chart showing concentrations of flavorants in an aerosol for an e-liquid aerosolized at different temperatures.

Lower temperature heating generally volatilizes less flavorant as compared with conventional e-cigarette atomization (high temperature). FIG. 2C illustrates experimental results showing the reduced effectiveness of low temperature heating of flavored e-liquids for volatilizing flavorants under common-use vaping topography (e.g., between about 70-150° C.). Accordingly, the aerosol produced by the two-stage e-cigarette 200 can be less flavored than directly atomized e-liquid. The aerosol of the two-stage e-cigarette 200 can be less desirable for the user.

Figure 2E:
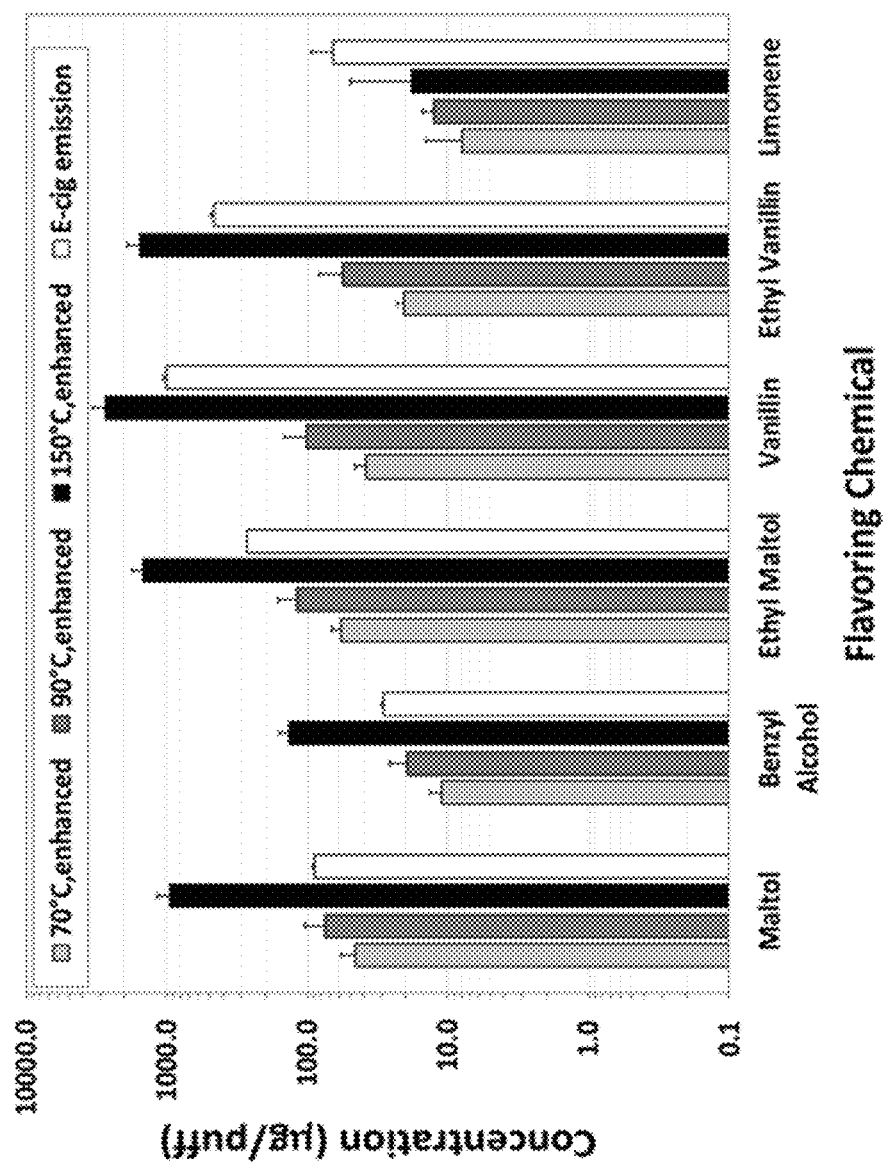
FIG. 2E is a chart showing concentrations of flavorants in an aerosol for a flavorant enhanced e-liquid aerosolized at different temperatures.

In response to this problem of low-flavorant delivery at low temperatures, another aspect of the present disclosure is the use of enhanced-concentration e-liquids. As shown in the table in FIG. 2D, additional flavorant can be included in the flavored e-liquid relative to conventional flavored e-liquids. When used in the two-stage e-cigarette 200, these enhanced e-liquids can produce an aerosol that includes amounts of flavorant comparable to conventional atomization processes for conventional e-liquids (e.g., e-cigarette 100), as shown in FIG. 2E. FIG. 2D further includes acceptable ranges of enhanced concentrations for each of the listed flavorants.

Figure 2F:
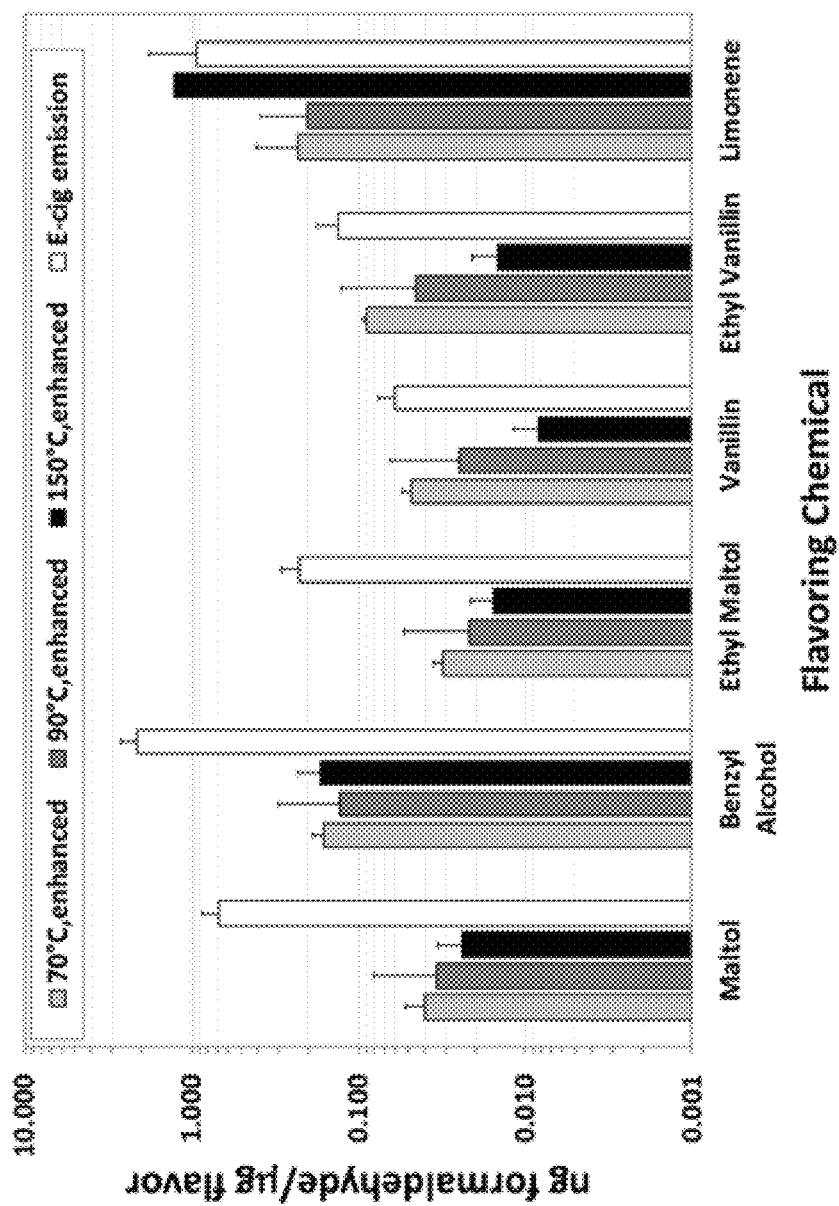
FIG. 2F is a chart showing a ratio of formaldehyde to flavorant concentrations for a flavorant enhanced e-liquid aerosolized at different temperatures.

With reference back to FIG. 2B, the use of enhanced-concentration e-liquids does increase the overall production of formaldehyde and acetaldehyde, based on experimental results. Nonetheless, the aerosol of the two-stage e-cigarette 200 using the enhanced-concentration e-liquids generally displays an overall reduction in the ratio of formaldehyde concentration to flavor concentration as shown in FIG. 2F. Accordingly, the e-cigarette 200 provides both a reduced amount of harmful chemicals and a desirable flavor profile.

In accordance with one or more aspects of the present disclosure, provided is an apparatus comprising: a carrier reservoir configured to store a carrier liquid; an atomizer configured to aerosolize the carrier liquid into an aerosol; a power source configured to provide an electrical current to the atomizer; a flavorant reservoir configured to store a flavorant liquid; an air channel extending from the carrier reservoir to the flavorant reservoir and from the flavorant reservoir to a mouthpiece, the air channel configured to provide an airway for delivering the aerosol via the mouthpiece to a user; and a delivery mechanism chamber configured to expose the flavorant liquid to the air channel. In related aspects, the delivery mechanism chamber may be positioned downstream of the atomizer along the air channel.

In accordance with one or more aspects of the present disclosure, provided is an apparatus comprising: a first chamber configured to store a carrier liquid, the carrier liquid free of flavorants; a second chamber located proximal relative to the first reservoir and connected to the first reservoir via a first channel comprising a first aerosol nozzle, the second chamber configured to store a flavorant liquid; and a mouthpiece located proximal relative to the second chamber and connected to the second chamber via a second channel comprising a second aerosol nozzle. In related aspects, the first chamber may comprise an atomizer coupled to the first reservoir and configured to, in use, aerosolize the carrier liquid into an aerosol that passes through the first aerosol nozzle of the first channel to the second chamber. In further related aspect, the second chamber may be configured to, in use, receive the aerosol from the first chamber and expose the aerosol to the flavorant liquid to generate a flavored aerosol that passes through the second aerosol nozzle of the second channel to the mouthpiece.

Figure 3:
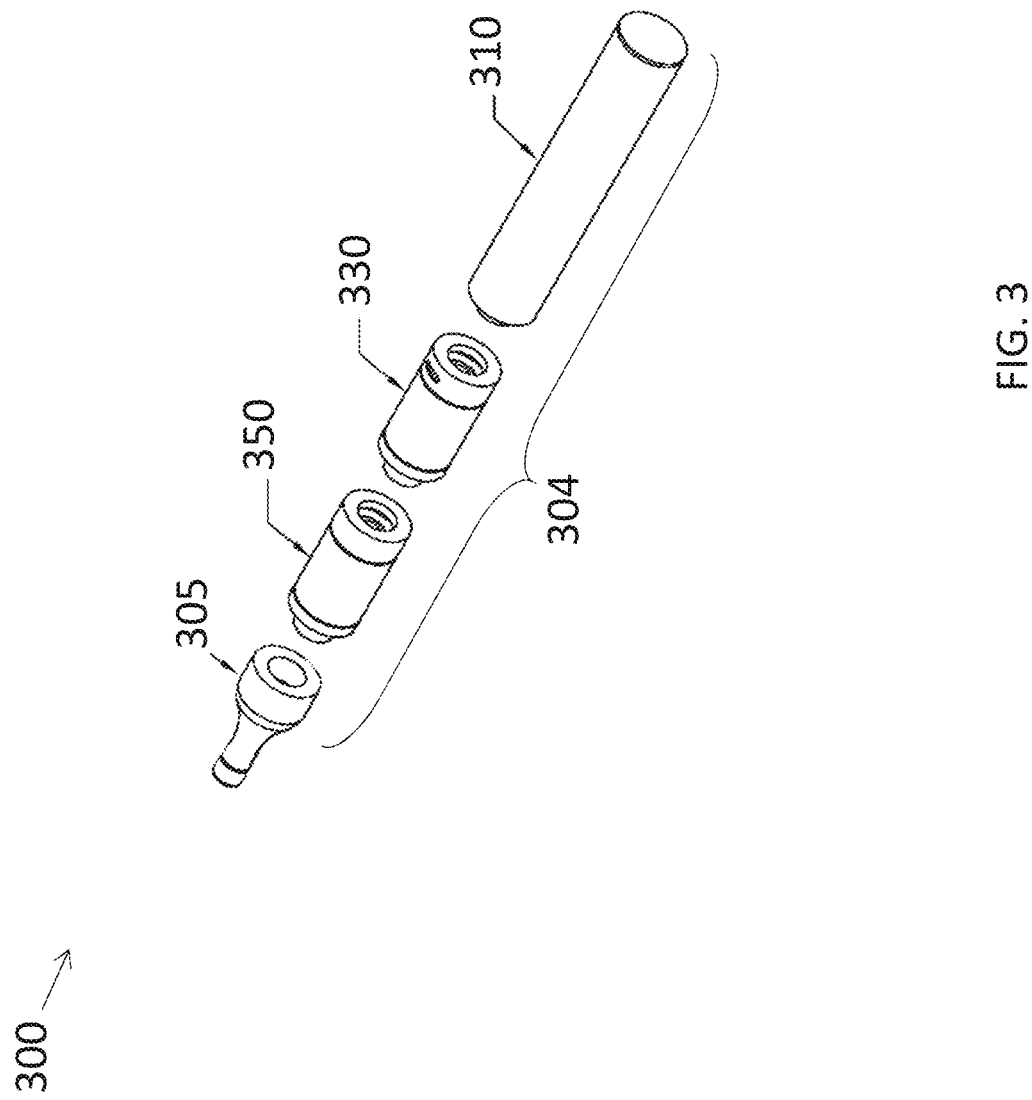
FIG. 3 is an implementation of an e-cigarette.

FIG. 3 illustrates an implementation of an e-cigarette 300. The e-cigarette 300 can have components similar to the schematic implementation of e-cigarette 200 in FIG. 2B. The e-cigarette 300 can include a housing 304. In some implementations, the housing 304 can be modular. The components of the housing 304 can be purchased individually and assembled together into the housing 304. The components of the housing 304 can have one or more standardized connections, such as male and female connections for attachment with adjacent components of the housing 304.

The housing 304 can include a battery assembly 310, a first module 330, a second module 350, and/or a mouthpiece 305. The mouthpiece 305 can be connected with the second module 350. The second module 350 can be connected with the first module 330. The first module 330 can be connected with the battery assembly 310. Although this order of connection is disclosed, other combinations and orders of the components of the housing 304 are also possible.

Figure 4:
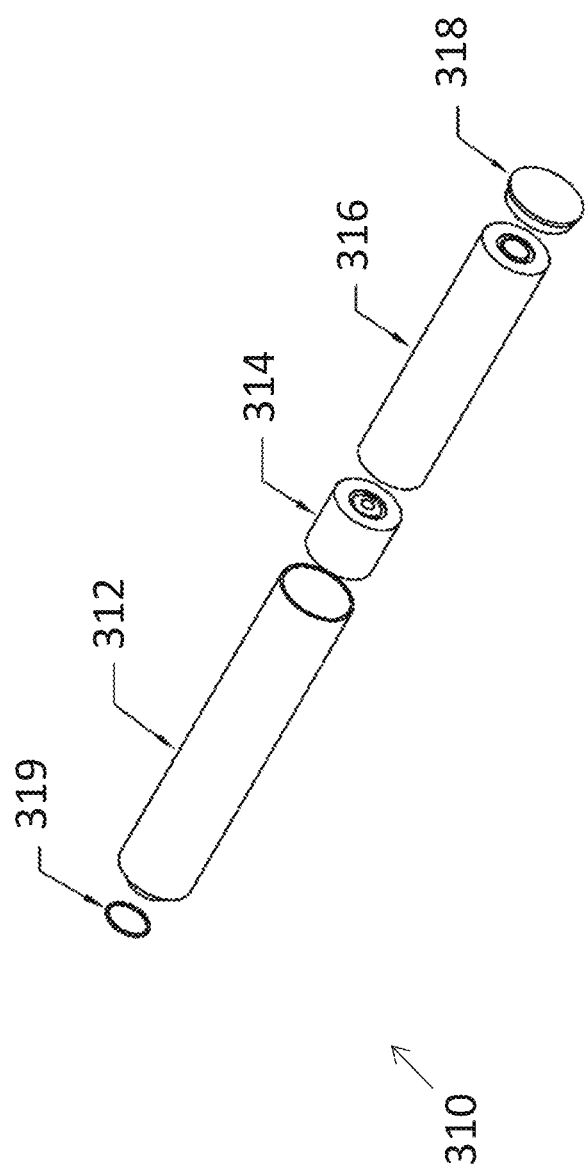
FIG. 4 is an exploded view of a battery assembly of the e-cigarette of FIG. 3.

With reference to FIG. 4, the battery assembly 310 can include a battery housing 312. One end of the battery housing 312 can be configured to be connected with the first module 330. The battery housing 312 can be a generally cylindrical sleeve. The battery housing 312 can have an interior cylindrical section for housing a battery 316. The battery 316 can be a conventional battery such as a rechargeable lithium ion battery or other battery type. In some implementations, the battery 316 can be permanently fixed within the battery housing 312. In other implementations, the battery 316 can be replaceable. The battery housing 312 can include an end cap 318. The end cap 318 can connect with an end of the battery housing 312 opposite the connection with the first module 330. The cap 318 can be removable and used to insert the battery and other components into the housing 312.

The battery assembly 310 can include a controller 314. The controller 314 can alternatively or additionally be included in other portions of the housing 304. In some implementations, the controller 314 is used in conjunction with one or more buttons or user inputs. The controller 314 can be configured to deliver power to an atomizer as described further below in conjunction with the first module 330. The controller 314 can optionally include or be used in conjunction with one or more pressure sensors for sensing a draw of air from the user. The pressure sensors can activate the controller 314 to deliver energy to the atomizer system. The battery housing 312 can include a seal to prevent contamination and/or liquids or aerosol from entering into the battery housing 312. The seal 319 can be located at the connection between the first module 330 and the battery assembly 310. Although the battery housing 312 is shown and described as a cylindrical sleeve, other shapes are also contemplated herein.

Figure 6:
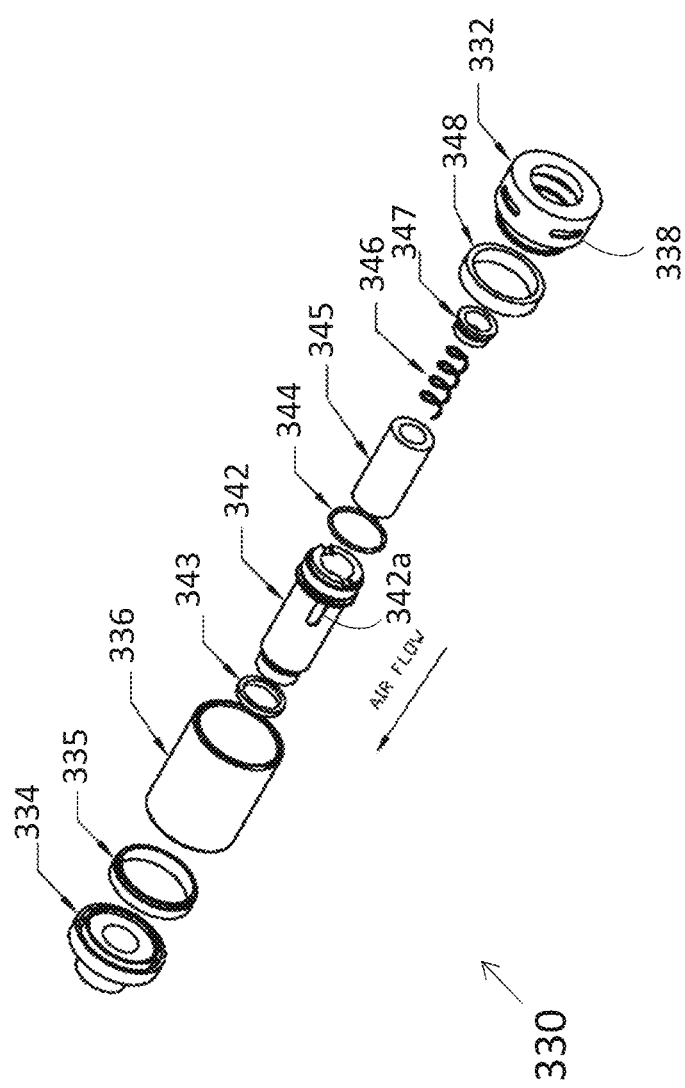
FIG. 6 is an exploded view of the first module of the FIG. 3.

With reference to FIGS. 5A-6, the first module 330 can include a first end 332 and a second end 334. The first end 332 can be configured to be coupled with the battery assembly 310. The first end 332 can include one or more connections such as threaded connections and/or one or more electrical contacts for delivering energy from the battery 316 into the first module 330. The first module 330 can include an outer housing 336. The second end 334 can be configured to be coupled with the second module 350. The first end 332 can include one or more air inlets 338 for delivering air along an airway 340. The airway 340 can extend through the first module 330.

The first module 330 can include the outer housing 336. Inside the outer housing 336 there can be an inner chamber member 342. Between the outer housing 336 and the inner chamber member 342, there can be a first e-liquid reservoir 337. The reservoir 337 can be configured to hold an e-liquid. The e-liquid can be modified from a conventional e-liquid in that it includes no or substantially no flavorants. The inner chamber member 342 can define an inner chamber 341. The airway 340 can pass through the inner chamber 341. One end of the inner chamber 341 can include a nozzle 347 through which air can enter the inner chamber 341. The inner chamber member 342 can include one or more apertures 342a through which the e-liquid in the reservoir 337 can pass (e.g., into the inner chamber 341). Inside the inner chamber 341 can be a porous media 345. The porous media 345 can act as a sponge or permeable material or a wick-like material for delivering the e-liquid into adjacent with and/or adjacent with a heating element 346.

The heating element 346 can be located within the inner chamber 341. The heating element 346 can be in the form of a coil or other suitable shape for a heating element. The heating element 346 can be in electrical connection with the battery assembly 310 through the first end 332 of the housing 336 and the electrical connections thereof. The heating element 346 in conjunction with the porous media 345 can act as an atomizer to aerosolize the e-liquid of the reservoir 337.

The outer housing 336 can include a seal 335 between the second end 334 and the outer housing 336. A second seal 348 can be located between the first end 332 and the outer housing 336. In this manner, the reservoir 337 can be sealed on either end. The inner chamber member 342 can include first and second seals 343, 344 on either end thereof.

The airway 340 can pass through within the first module 330 and be in communication with the air inlets 338. The airway 340 can pass directly through the inner chamber 341 and into communication with the heating element 346 and the porous media 345. The airway 340 can terminate at the mouthpiece 305. Ambient air can be drawn in through the air inlets 338 and along the airway 340 when a user draws at the mouthpiece 305. The first module 330 can function to produce an aerosol within the inner chamber 341 by use of energy from the battery assembly 310 at the heating element 346. Heating of the heating element 346 can be actuated automatically, such as by a user drawing at the mouthpiece and pressure drop being sensed by the controller 314, or initiated by the user operating a button or other mechanism for turning on the heating element and beginning the atomization process. The aerosol formed in the first module 330 can pass along the airway 340 into the second module 350.

The e-liquid used in conjunction with the first reservoir 337 is different from a commercially sold e-liquid in that it does not contain flavorants chemicals. Thus, by leaving out flavorants from the e-liquid, there can be a reduced amount of harmful secondary chemical such as carbonyls that form by the atomization of the first module 330. The e-liquid can include nicotine and/or nicotine salts.

Figure 7A:
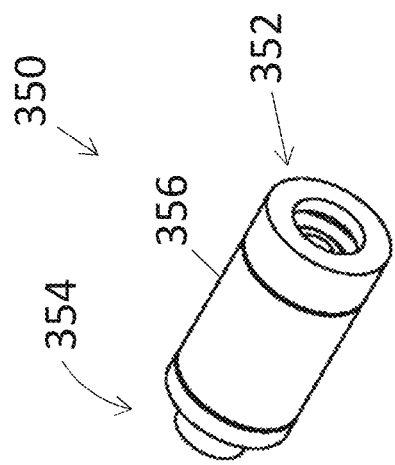
FIG. 7A is a perspective view of a second module of the e-cigarette of FIG. 3.
Figure 7B:
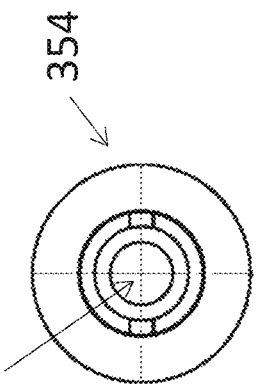
FIG. 7B is an end view of the second module of FIG. 7A.
Figure 7D:
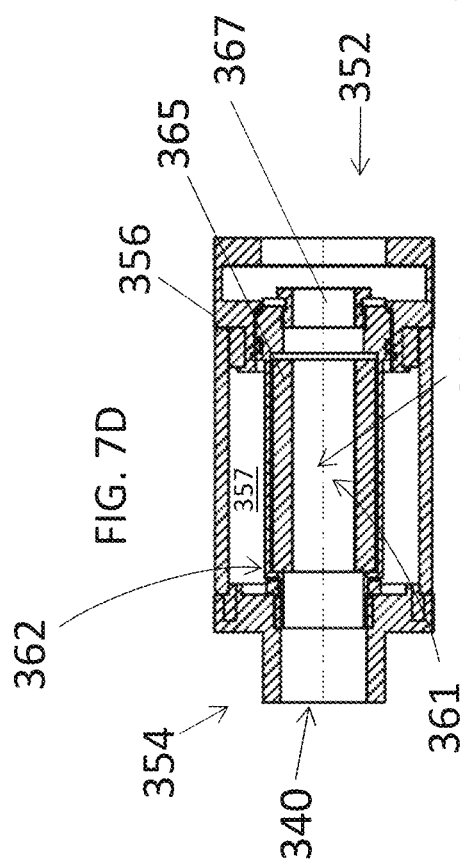
FIG. 7D is a section view taken along the line 7D-7D in FIG. 7C.
Figure 7C:
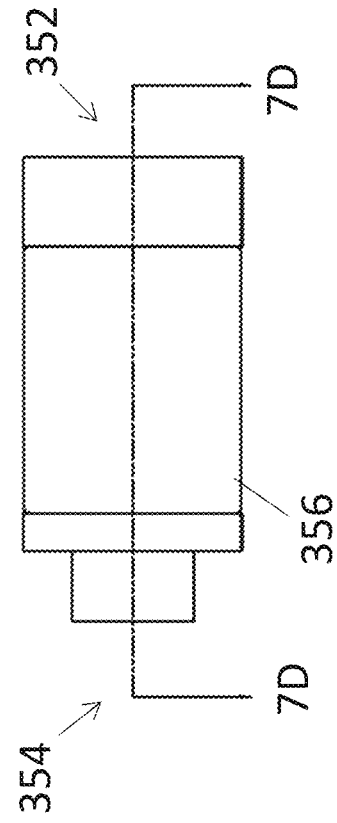
FIG. 7C is a side view of the second module of FIG. 7A.
Figure 8:
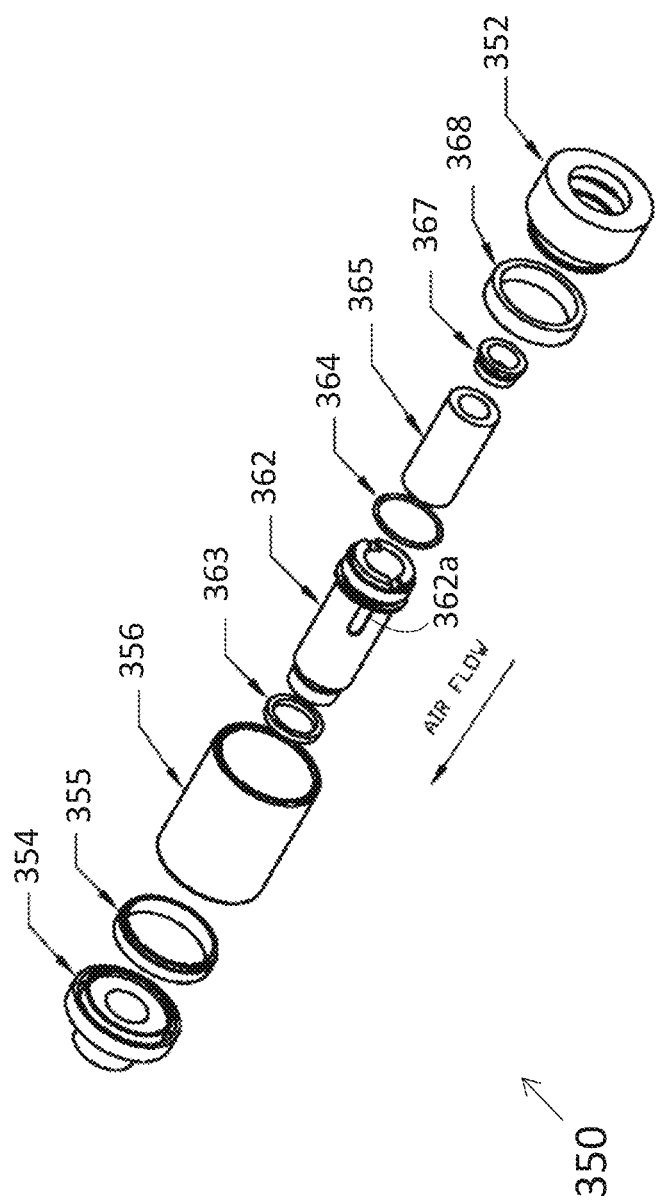
FIG. 8 is an exploded view of the second module of FIG. 7A.

With reference to FIGS. 7A-8, the second module 350 can include an outer housing 356. The outer housing 356 can be generally cylindrical or any other shape. The outer housing 356 can include a first end 352 and a second end 354. The first end 352 can be configured to be connected with the second end 334 of the first module 330 such as by one or more threaded or other type of connections. These threaded connections can be standardized in a modular fashion. The second end 354 can be connected with the mouthpiece 305 by one or more threaded or other connection types. The second module 350 can include an inner chamber member 362 defining or at least partially defining an inner chamber 361. The inner chamber 361 can include a nozzle 367. The nozzle 367 can include an inner cutout to form a portion of the airway 340. The nozzle 367 can be upstream of the second end 354 along the airway 340. The airway 340 can be in fluid communication with the inner chamber 361 through the nozzle 367.

Between the outer housing 356 and the inner chamber member 362 there can be a flavorant reservoir 357. The flavorant reservoir 357 can contain a flavored e-liquid. The flavored e-liquid can include any or all of the flavorants listed above and in FIG. 2D. The flavored e-liquid can also include any of the standard ingredients noted above for an e-liquid. Optionally, the concentration of flavoring chemicals in the flavored e-liquid contained in the reservoir 357 can be higher than a conventional e-liquid such as shown in FIG. 2D (e.g., a flavorant enhanced e-liquid). This can be necessary because of the reduced temperatures used volatilizing the e-liquid. The flavored e-liquid can omit nicotine and/or nicotine salts. The flavored e-liquid can be in the form of a liquid, a gel or other form.

The inner chamber member 362 can include one or more pathways 362a (e.g., apertures) through which the flavored e-liquid can seep into the inner chamber 361 (e.g., from the flavorant reservoir 357). A delivery mechanism 365 can be located at least partially or fully inside the inner chamber 361. The inner chamber member 362 include one or more apertures, wicks, or other conduits to fill the delivery mechanism 365 with flavored e-liquid from the flavorant reservoir 357. The delivery mechanism 365 can comprise a sleeve. The sleeve can be cylindrical or any other shape. An outer surface of the sleeve can engage with an inner surface of the inner chamber member 362. The delivery mechanism 365 can comprise a porous media. The delivery mechanism 365 can comprise a diffusing material such as a foam, a sponge, or other permeable membrane. The delivery mechanism 365 can comprise a plastic, rubber, cellulose, wood pulp, fibrous material (synthetic or natural), mineral, metallic and/or any other suitable material. The delivery mechanism 365 can comprise a smooth inner surface of the inner chamber member 362, a textured inner surface of the inner chamber member 362, and/or one or more grooves or slots.

The delivery mechanism 365 can contain the flavored e-liquid. The delivery mechanism 365 can be located in communication with the airway 340. The airway 340 can pass through the sleeve of the delivery mechanism 365. The airway 340 can extend from the first module 330 through the second module 350 through the nozzle 367 and/or the chamber 361. The airway 340 can follow a tortuous path through the inner chamber 361 (e.g., through the sleeve). The delivery mechanism 365 can include one or more pathways therethrough. The delivery mechanism 365 can include a porous or honeycombed structure.

The airway 340 can carry the heated aerosol from the first module 330 into contact with the delivery mechanism 365 containing the flavored e-liquid. This contact can cause at least some of the flavored e-liquid to volatilize or otherwise be carried into the passing aerosol. The delivery mechanism 365 can increase the total surface area of the flavored e-liquid exposed to the heater aerosol (e.g., relative to the cross section of the pathway 362 or the inner surface of the inner chamber member 362). The aerosol can pass through the inner chamber 361 of the second module 350 towards the mouthpiece 305 to be inhaled by a user having picked up flavorants from the delivery mechanism 365.

The outer housing 356 can be connected with the first end 354 and include one or more seals 355 to secure the reservoir 357 against leakage. At the opposite end 352 there can also be a seal 368 sealing between the outer housing 356 and the first end 352. Either end of the inner chamber member 362 can include seals 363, 364 for sealing opposite sides of the flavoring reservoir 357. In some implementations, the second module 350 can include one or more additional air inlets (not shown) for cooling of the aerosol within the second module 350. The additional air inlets can be configured to draw in less ambient air than the air inlets 338 to prevent over cooling the aerosol.

Figure 9:
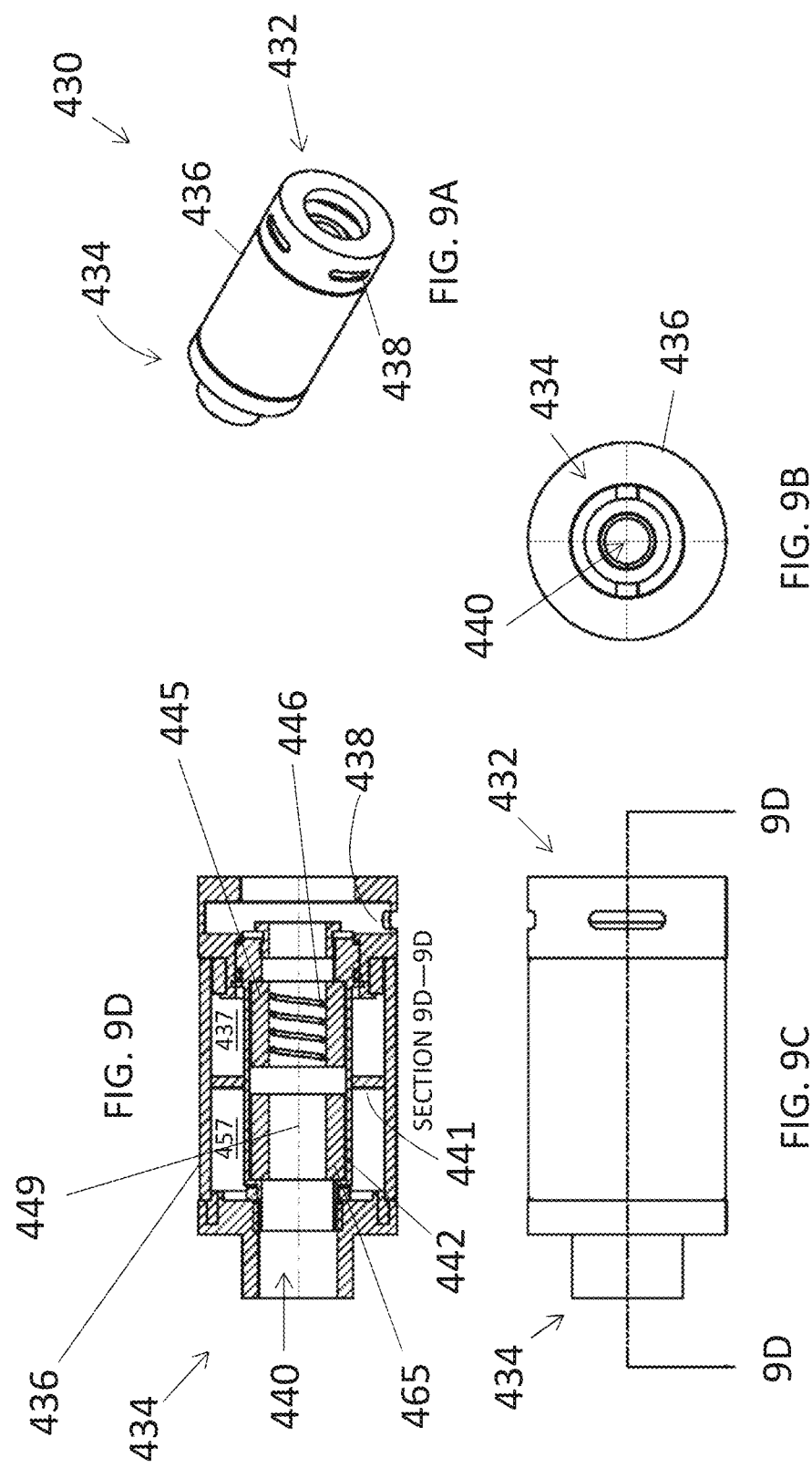
FIG. 9A is a perspective view of another chamber for the e-cigarette of FIG. 3.
FIG. 9B is an end view of the chamber of FIG. 9A.
FIG. 9C is a side view of the chamber of FIG. 9A.
FIG. 9D is a section view taken along the line 9D-9D in FIG. 9C.
Figure 10:
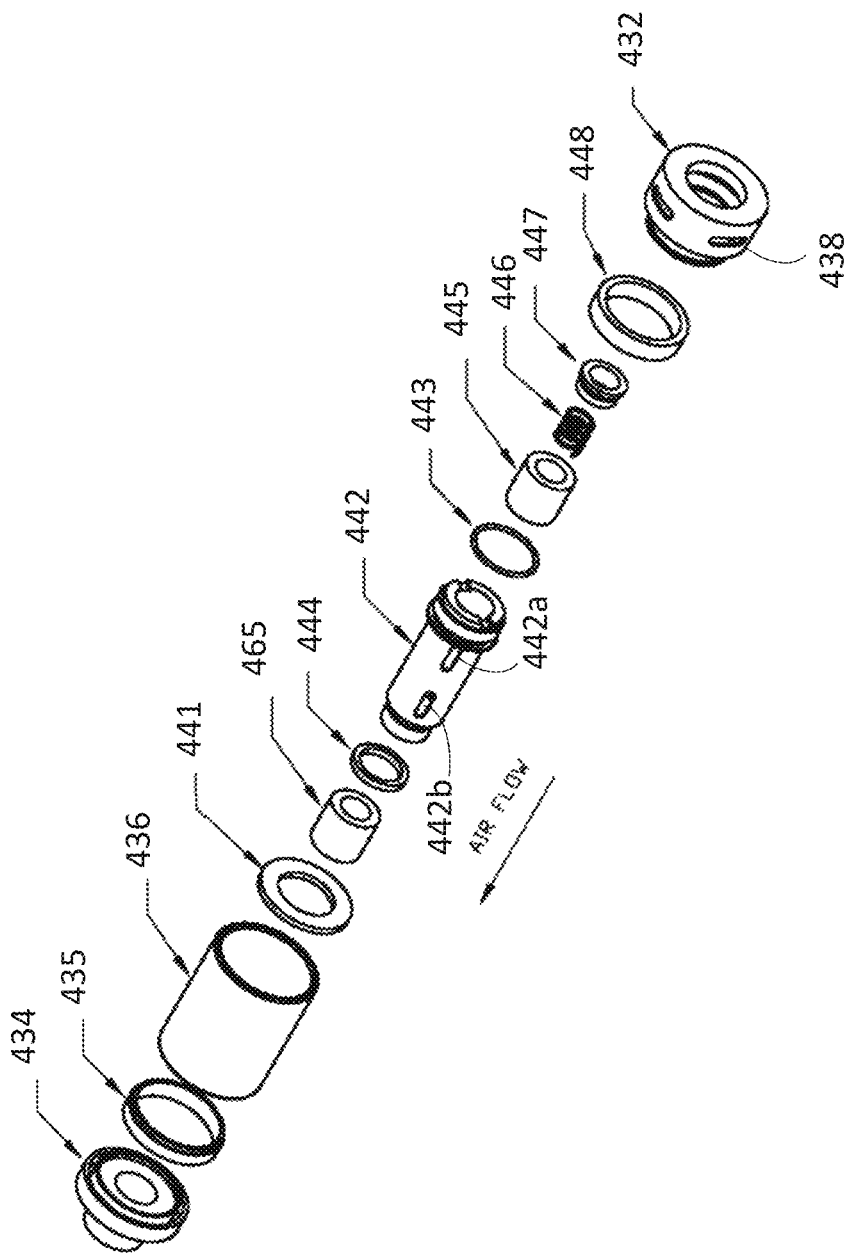
FIG. 10 is an exploded view of the chamber of FIG. 9A.

With reference to FIGS. 9A-10, another implementation of a combination module 430 for an e-cigarette design is shown. The combination module 430 can generally combine the functionality of the first module 330 and the second module 350. Thus, in some implementations of the e-cigarette 300, the e-cigarette 300 includes a single module containing multiple reservoirs for a substantially flavor-free e-liquid and a flavored e-liquid.

The combination module 430 can include a first end 432. The first end 432 can include a coupling for connection with the battery module 310. The coupling at the first end 432 can be standardized and include one or more threads and/or battery connections for transmitting power into the atomization chamber therein. A first end 432 can include one or more inlet apertures 438 to provide access for ambient air to pass into an airway 440 extending through the combination module 430. A second end 434 of the combination module 430 can be configured to connect with the mouthpiece 305 or another chamber module.

An outer housing 436 of the module can connect between the first and second ends 432, 434. The outer housing 436 can be generally cylindrical shape but this is not required. The combination module 430 can include an inner chamber member 442. The inner chamber member 442 can be located within the outer housing 436. The inner chamber member 442 can at least partially define an inner chamber 449. A nozzle 447 can be located at one end of the inner chamber 449. The inner chamber member 442 can be coupled with a liquid partition 441. The liquid partition 441 can be a rubber or other non-permeable material that can extend between the inner chamber member 442 and the outer housing 436. The outer housing 436, the inner chamber member 432, and the liquid partition 441 can be assembled together to form a first reservoir 437 and a second reservoir 457. The first reservoir 437 can be configured to hold a flavorant-less e-liquid. The second reservoir 457 can be configured to hold a flavored e-liquid.

The flavorless e-liquid in the first reservoir 437 can be in communication with a first porous media 445 through one or more apertures 442a through the inner chamber member 442. The first porous media 445 can be in contact with or adjacent to a heated element 446. The heating element 446 can be coupled to one or more electrical connections with the battery module 310 for delivering energy to heat the heating element 446. Thus, the flavorless e-liquid in the first reservoir 437 can pass through the first porous media 445 and into contact with or adjacent to the heated element 446 which can be heated to produce an aerosol. The aerosol can be passed along the airway 440 by a user drawing ambient air into the airway 440 through the one or more inlets 438.

The second reservoir 457 contains the flavored e-liquid and can be in communication with a delivery mechanism 465 through one or more apertures 442b in the inner chamber member 442. The delivery mechanism 465 can have the same structure as the delivery mechanism 365. The flavored e-liquid can pass through the apertures 442b and be absorbed by the delivery mechanism 465 and thus into exposed to the aerosol and ambient air passing within the airway 440. As the heated aerosol passes along the airway 440, it can volatilize the flavored e-liquid held within the porous media and at least some of the flavored e-liquid can be aerosolized and carried along the airway to be inhaled by the user.

In some implementations, the first and second reservoirs 437, 457 can be approximately equal in size. In other implementations, depending on the positioning of the liquid partition member 441, the first and second reservoirs 437, 457 can be of unequal sizes. In some implementations, the first porous media 445 can be spaced or partitioned away from the second porous media 465. This can be advantageous where it is undesirable for any of the flavored e-liquid to be inadvertently heated by the heating element 446.

The combination module 430 can include a variety of seals or gaskets. A seal 435 can be located between the second end 434 and the outer housing 436. A seal 448 can be located between the first end 432 and the outer housing 436. A seal 443 can be coupled with one end of the inner chamber member 442 and a seal 444 can be coupled with the other end of the inner chamber member 442 to seal the first and second reservoirs 437, 457. The seals or gaskets and/or the liquid partition 441 can be made out of conventional gasket material, such as rubber silicone and similar materials.

Figure 11:
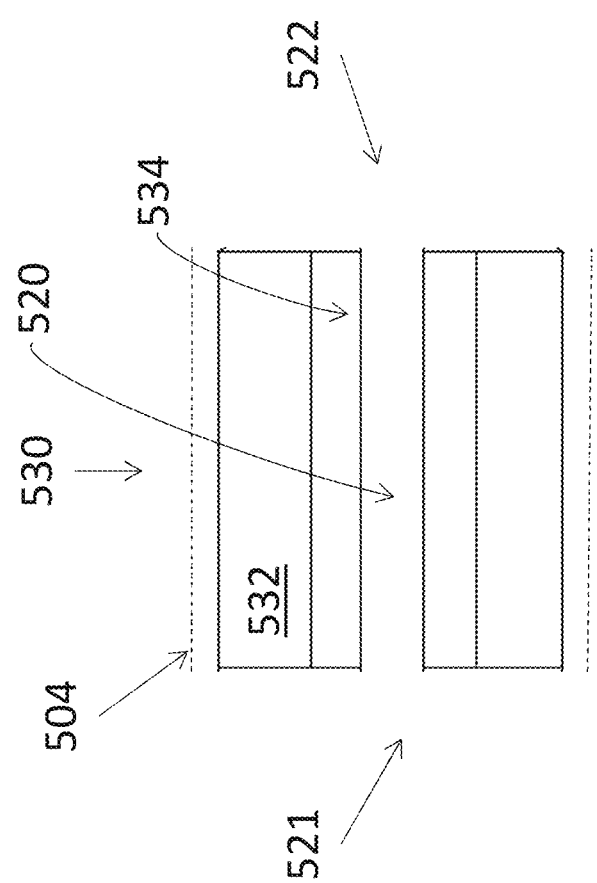
FIG. 11 is a schematic view of an implementation of an add-on module for an e-cigarette.

FIG. 11 illustrates one implementation of an add-on module 530 for adapting the conventional e-cigarette 100 to reduce harmful emissions associated with directly heating flavoring compounds. The module 530 can include first and second ends 521, 522. The first end 521 can include one or more couplings for connection with the e-cigarette (e.g., in place of a mouthpiece). The first end 521 can include a standardized coupling. The second end 522 may comprise a connection for a mouthpiece and/or the mouthpiece itself (not shown).

A housing 504 of the module 530 can include an airway 520. The airway 520 can extend from and/or align with the e-cigarette (e.g., from an atomizer thereof) to the mouthpiece. The module 530 can connect with the e-cigarette 100 downstream of the atomizer and before the mouthpiece 105. The module 530 can include a flavorant reservoir 532. The flavorant reservoir 532 can house a flavored e-liquid. The flavored e-liquid can include one or more carrier liquids and any or all of the flavorants: benzyl alcohol, ethyl maltol, vanillin, ethyl vanillin, limonene, and/or other flavorings. The flavored e-liquid in a flavorant 532 can include any of the carriers such as the propylene, glycol, vegetable glycerol, water, and/or ethanol.

The module 530 can include a delivery mechanism 534. The delivery mechanism 534 can be located adjacent to and/or within the airway 520. The delivery mechanism 534 can be a sponge-like material or other permeable material that can at least temporarily contain the flavored e-liquid and expose the flavored e-liquid to air and/or vapor passing through the airway 520 on its way to the mouthpiece. The module 530 can include one or more apertures, wicks, or other delivery mechanisms to fill the delivery mechanism 534 with flavored e-liquid from the reservoir 532. The delivery mechanism 534 can include the flavored e-liquid in the form of a gel or dissolved in a permeable membrane or substrate through which aerosol and/or air must pass along the airway 520. Optionally, the module 530 can include a second atomizer that operates at a reduced temperature than the atomizer of the e-cigarette (e.g., in the range of about 70° C. to about 150° C.). The delivery mechanism 534 need not be as thermally stable as the wick of the atomizer because it is generally exposed to lower temperatures.

The e-cigarette 100 can be filled with a substantially flavorant free e-liquid. Aerosol can be created by the atomizer thereof at an elevated temperature. The resulting aerosol can pass along the airway 520 into the module 530. The passage of the heated aerosol through the delivery mechanism 534 can volatilize the flavored e-liquid and thereby flavor the aerosol for inhalation by the user at the mouthpiece.

CERTAIN TERMINOLOGY

Terms of orientation used herein, such as "top," "bottom," "proximal," "distal," "longitudinal," "lateral," and "end," are used in the context of the illustrated implementation. However, the present disclosure should not be limited to the illustrated orientation. Indeed, other orientations are possible and are within the scope of this disclosure. Terms relating to circular shapes as used herein, such as diameter or radius, should be understood not to require perfect circular structures, but rather should be applied to any suitable structure with a cross-sectional region that can be measured from side-to-side. Terms relating to shapes generally, such as "circular," "cylindrical," "semi-circular," or "semi-cylindrical" or any related or similar terms, are not required to conform strictly to the mathematical definitions of circles or cylinders or other structures, but can encompass structures that are reasonably close approximations.

Conditional language, such as "can," "could," "might," or "may," unless specifically stated otherwise, or otherwise understood within the context as used, is generally intended to convey that certain implementations include or do not include, certain features, elements, and/or steps. Thus, such conditional language is not generally intended to imply that features, elements, and/or steps are in any way required for one or more implementations.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain implementations require the presence of at least one of X, at least one of Y, and at least one of Z.

The terms "approximately," "about," and "substantially" as used herein represent an amount close to the stated amount that still performs a desired function or achieves a desired result. For example, in some implementations, as the context may dictate, the terms "approximately," "about," and "substantially," may refer to an amount that is within less than or equal to 10% of the stated amount. The term "generally" as used herein represents a value, amount, or characteristic that predominantly includes or tends toward a particular value, amount, or characteristic. As an example, in certain implementations, as the context may dictate, the term "generally parallel" can refer to something that departs from exactly parallel by less than or equal to 20 degrees.

SUMMARY

Several illustrative implementations of e-cigarettes have been disclosed. Although this disclosure has been described in terms of certain illustrative implementations and uses, other implementations and other uses, including implementations and uses which do not provide all of the features and advantages set forth herein, are also within the scope of this disclosure. Components, elements, features, acts, or steps can be arranged or performed differently than described and components, elements, features, acts, or steps can be combined, merged, added, or left out in various implementations. All possible combinations and subcombinations of elements and components described herein are intended to be included in this disclosure. No single feature or group of features is necessary or indispensable.

Certain features that are described in this disclosure in the context of separate embodiments can also be implemented in combination in a single embodiment. Conversely, various features that are described in the context of a single implementation also can be implemented in multiple embodiments separately or in any suitable subcombination. Moreover, although features may be described above as acting in certain combinations, one or more features from a claimed combination can in some cases be excised from the combination, and the combination may be claimed as a subcombination or variation of a subcombination.

Any portion of any of the steps, processes, structures, and/or devices disclosed or illustrated in one implementation or example in this disclosure can be combined or used with (or instead of) any other portion of any of the steps, processes, structures, and/or devices disclosed or illustrated in a different implementation, flowchart, or example. The implementations and examples described herein are not intended to be discrete and separate from each other. Combinations, variations, and some implementations of the disclosed features are within the scope of this disclosure.

While operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Additionally, the operations may be rearranged or reordered in some implementations. Also, the separation of various components in the implementations described above should not be understood as requiring such separation in all implementations, and it should be understood that the described components and systems can generally be integrated together in a single product or packaged into multiple products. Additionally, some implementations are within the scope of this disclosure.

Further, while illustrative embodiments have been described, any implementations having equivalent elements, modifications, omissions, and/or combinations are also within the scope of this disclosure. Moreover, although certain aspects, advantages, and novel features are described herein, not necessarily all such advantages may be achieved in accordance with any particular implementation. For example, some implementations within the scope of this disclosure achieve one advantage, or a group of advantages, as taught herein without necessarily achieving other advantages taught or suggested herein. Further, some implementations may achieve different advantages than those taught or suggested herein.

Some implementations have been described in connection with the accompanying drawings. The figures are drawn and/or shown to scale, but such scale should not be limiting, since dimensions and proportions other than what are shown are contemplated and are within the scope of the disclosed invention. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various implementations can be used in all other implementations set forth herein. Additionally, any methods described herein may be practiced using any device suitable for performing the recited steps.

For purposes of summarizing the disclosure, certain aspects, advantages and features of the inventions have been described herein. Not all, or any such advantages are necessarily achieved in accordance with any particular implementation of the inventions disclosed herein. No aspects of this disclosure are essential or indispensable. In many implementations, the devices, systems, and methods may be configured differently than illustrated in the figures or description herein. For example, various functionalities provided by the illustrated modules can be combined, rearranged, added, or deleted. In some implementations, additional or different processors or modules may perform some or all of the functionalities described with reference to the example implementation described and illustrated in the figures. Many implementation variations are possible. Any of the features, structures, steps, or processes disclosed in this specification can be included in any implementation.

In summary, various implementations and examples of e-cigarette systems and related methods have been disclosed. This disclosure extends beyond the specifically disclosed implementations and examples to other alternative implementations and/or other uses of the implementations, as well as to certain modifications and equivalents thereof. Moreover, this disclosure expressly contemplates that various features and aspects of the disclosed implementations can be combined with, or substituted for, one another. Accordingly, the scope of this disclosure should not be limited by the particular disclosed implementations described above, but should be determined only by a fair reading of the claims.

The invention claimed is:

1. An e-cigarette, comprising:
a carrier reservoir configured to store a carrier liquid;
an atomizer configured to aerosolize the carrier liquid into an aerosol;
a power source configured to provide an electrical current to the atomizer;
a flavorant reservoir configured to store a flavorant liquid;
an air channel extending from the carrier reservoir to the flavorant reservoir and from the flavorant reservoir to a mouthpiece, the air channel configured to provide an airway for delivering the aerosol via the mouthpiece to a user; and
a delivery mechanism formed by a diffusing material configured to expose the flavorant liquid to the air channel, the diffusing material positioned between the flavorant reservoir and the air channel;

wherein the delivery mechanism is positioned downstream of the atomizer along the air channel.

2. The e-cigarette of claim 1, wherein passage of the aerosol through the delivery mechanism aerosolizes the flavorant liquid into the aerosol.

3. The e-cigarette of claim 1, wherein the carrier liquid is aerosolized at a first temperature and the flavorant liquid is aerosolized at a second temperature, the second temperature being below the first temperature.

4. The e-cigarette of claim 1, further comprising a first module containing the atomizer for aerosolizing the carrier liquid at a first temperature.

5. The e-cigarette of claim 1, wherein:

the power source comprises a battery, and the flavorant reservoir, the carrier reservoir, and the battery are modular and attachable by one or more threaded connections.

6. The e-cigarette of claim 1, wherein the carrier liquid comprises at least one of propylene glycol, vegetable glycerin, nicotine, water, and ethanol.

7. The e-cigarette of claim 1, wherein the flavorant liquid comprises at least one of maltol, benzyl alcohol, ethyl maltol, vanillin, ethyl vanillin, and limonene.

8. The e-cigarette of claim 1, wherein the flavorant liquid is a gel.

9. The e-cigarette of claim 1, wherein less than 30 nanograms of formaldehyde per puff are produced for a common-use vaping topography.

10. The e-cigarette of claim 1, wherein the carrier liquid is substantially free of flavorants.

11. The e-cigarette of claim 1, wherein the diffusing material surrounds at least a portion of the air channel between the atomizer and the mouthpiece.

12. The e-cigarette of claim 1, further comprising an inner wall member separating the flavorant reservoir from the diffusing material, the inner wall member including at least one aperture through which the flavored e-liquid can seep into the delivery mechanism formed by the diffusing material.

13. The e-cigarette of claim 3, wherein aerosolizing the flavorant liquid at the second temperature reduces the formation of at least one of formaldehyde, acetaldehyde, and acrolein relative to aerosolizing the flavorant liquid at the first temperature.

14. The e-cigarette of claim 4, further comprising a second module containing the flavorant reservoir.

15. The e-cigarette of claim 14, wherein the second module and the first module can be assembled together by one or more couplings.

16. An e-cigarette, comprising:
a carrier reservoir configured to store a carrier liquid;
an atomizer configured to aerosolize the carrier liquid into an aerosol;
a power source configured to provide an electrical current to the atomizer;
a flavorant reservoir configured to store a flavorant liquid;

an air channel extending from the carrier reservoir to the flavorant reservoir and from the flavorant reservoir to a mouthpiece, the air channel configured to provide an airway for delivering the aerosol via the mouthpiece to a user; and a delivery mechanism formed by a diffusing material configured to expose the flavorant liquid to the air channel;

wherein the delivery mechanism is positioned downstream of the atomizer along the air channel; and the delivery mechanism comprises a sleeve configured to wick the flavorant liquid, and the aerosol passes through at least a portion of the sleeve along the airway.

17. The e-cigarette of claim 16, wherein the sleeve comprises a porous material.

18. The e-cigarette of claim 16, wherein the air channel comprises a tortuous path through the delivery mechanism.

19. The e-cigarette of claim 16, wherein the delivery mechanism comprises a honeycombed structure.

20. A flavorant reservoir module of an e-cigarette, comprising:
a chamber having a first end and a second end, the first end configured to couple with an atomizer and house a flavorant liquid separately from the atomizer;

a flavorant reservoir configured to house the flavorant liquid ; and an air channel configured to accommodate an aerosol flow through the chamber, the first and second ends of the chamber located along the air channel;

wherein a delivery mechanism formed by a diffusing material is positioned between the flavorant reservoir and the air channel, the diffusing material configured to expose the flavorant liquid to the air channel.

21. The module of claim 20, wherein the air channel is surrounded by the diffusing material.

22. An apparatus, comprising:
a first chamber configured to store a carrier liquid, the carrier liquid free of flavorants;

a second chamber located proximal relative to the first reservoir and connected to the first reservoir via a first channel comprising a first aerosol nozzle, the second chamber configured to store a flavorant liquid; and a mouthpiece located proximal relative to the second chamber and connected to the second chamber via a second channel comprising a second aerosol nozzle;

wherein the first chamber comprises an atomizer coupled to the first reservoir and configured to, in use, aerosolize the carrier liquid into an aerosol that passes through the first aerosol nozzle of the first channel to the second chamber;

wherein the second chamber is configured to, in use, receive the aerosol from the first chamber and expose the aerosol to the flavorant liquid to generate a flavored aerosol that passes through the second aerosol nozzle of the second channel to the mouthpiece;

wherein the second chamber includes an inner wall member that separates the flavorant liquid from the second channel, the inner wall member including at least one aperture through which the flavored e-liquid can seep into a delivery mechanism formed by a diffusing material.

* * * * *